United States Patent
Baker et al.

(10) Patent No.: US 6,799,071 B2
(45) Date of Patent: Sep. 28, 2004

(54) METHOD AND APPARATUS FOR SAFELY DISABLING RUNAWAY PACING PROTECTION IN A CARDIAC RHYTHM MANAGEMENT DEVICE

(75) Inventors: Kenneth L. Baker, Shoreville, MN (US); David Ternes, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 379 days.

(21) Appl. No.: 10/123,596

(22) Filed: Apr. 16, 2002

(65) Prior Publication Data

US 2003/0195573 A1 Oct. 16, 2003

(51) Int. Cl.$^7$ .................................................. A61N 1/37
(52) U.S. Cl. ................................................ 607/27; 607/28
(58) Field of Search ........................... 607/4, 9, 27–28

(56) References Cited

U.S. PATENT DOCUMENTS

| | | | | |
|---|---|---|---|---|
| 4,830,006 A | * | 5/1989 | Haluska et al. ................ 607/4 |
| 5,129,392 A | * | 7/1992 | Bardy et al. .................... 607/2 |
| 5,653,737 A | * | 8/1997 | van Lake ........................ 607/9 |
| 6,453,197 B1 | * | 9/2002 | Parry et al. .................... 607/14 |

OTHER PUBLICATIONS

Beginner's Corner "Watchdog Timers" by Niall Murphy and Michael Barr, *Embedded Systems Programming*, Oct. 2001.

* cited by examiner

*Primary Examiner*—Carl Layno
(74) *Attorney, Agent, or Firm*—Thomas J. Nikolai; Nikolai & Mersereau, P.A.

(57) ABSTRACT

As a safety feature for a cardiac rhythm management device in which a runaway protection feature may be disabled to allow programmed electrical stimulation and/or burst pacing to evaluate the device's ability to rein in an induced episode of tachycardia, a circuit is provided to automatically re-enable the runaway protection feature not only upon a software fault being detected, but also upon the lapse of a predetermined time interval.

12 Claims, 2 Drawing Sheets

METHOD AND APPARATUS FOR SAFELY DISABLING RUNAWAY PACING PROTECTION IN A CARDIAC RHYTHM MANAGEMENT DEVICE

BACKGROUND OF THE INVENTION

I. Field of the Invention

This invention relates generally to cardiac rhythm management devices, including pacemakers and automatic implantable cardiac defibrillators, and more particularly to a safety feature that comes into play when it is desired to disable the runaway protection feature of such devices.

II. Discussion of the Prior Art

For many years now, implantable cardiac pacers and pacer/defibrillators have incorporated a runaway protection capability that prevents the device from pacing the heart at an inordinately high rate due either to a software or a hardware fault. A runaway pacemaker is a pacemaker malfunction that may occur in single-chamber or multi-chamber pacing systems. It is usually the result of a minimum of at least two separate component failures within the pulse generator. The result is the rapid delivery of pacing stimuli to the heart, with the potential for inducing lethal arrhythmias, such as ventricular tachycardia or fibrillation. Newer devices incorporate a runaway protect circuit that prevents stimulation above a preset rate, typically between 180 and 200 bpm. Although somewhat rare, with modern pacing devices, this represents a medical emergency. Prompt surgical intervention to replace the device or, if all else fails, cutting the leads must be performed. This is most serious for a patient who may be pacemaker dependent.

As those skilled in the art appreciate, in antitachycardia pacing, it is often desirable to apply high frequency bursts of stimulating pulses in an attempt to induce an episode of tachycardia so that the capabilities of the device in terminating the episode can be evaluated. This requires that the runaway protection logic of the device be disabled, thus allowing stimulation at rates above the runway protection limit. However, disabling the runaway protection feature of a cardiac rhythm management device is inherently unsafe to do. Should the firmware lose control of the process due to a hardware or a firmware fault, the device may operate without runaway protection for an indefinite amount of time.

Accordingly, there is a need for a way to more safely disable the runaway protection feature of an implantable cardiac rhythm management device that will insure that it is automatically re-enabled within a set time following its being disabled. The present invention provides a logic arrangement for achieving this end.

SUMMARY OF THE INVENTION

A cardiac rhythm management device in accordance with the present invention comprises an R-wave sensor for sensing ventricular depolarization events, a P-wave sensor for sensing atrial events and a pulse generator for applying cardiac stimulating pulses to the heart of a patient. It further includes a programmed microprocessor-based controller that is coupled to the R-wave sensor to the P-wave sensor and to the pulse generator for providing stimulating pulses to the heart at times determined by the microprocessor-based controller. The microprocessor-based controller incorporates a programmable upper rate limit for normally precluding the pulse generator from applying the stimulating pulses to the heart at a rate greater than the established upper rate limit. The software, executable by the microprocessor-based controller, permits selective disabling of the runaway protection limit. In further accordance with the present invention, means are provided that are responsive to the selective disabling of the runaway protection limit and for automatically re-enabling the runaway protection limit a predetermined time following the disabling of the runaway protection limit.

In accordance with a further feature of the invention, this last mentioned means preferably comprises a first timer comprising a counter for counting regularly occurring clock or pacing pulses and for producing a runaway protection re-enabling signal when a predetermined time interval represented by the count value in the first counter reaching a predetermined value has elapsed. Under software control, however, the first counter may be reset before the first predetermined count value is reached to thereby extend the time interval that the runaway protection remains disabled. A second timer, also a counter for counting regularly occurring clock or pacing pulses is used to produce a signal to re-enable the runaway protection upon reaching a second predetermined count value, irrespective of the count state of the first counter. In this fashion, the length of the interval during which fast pacing may take place can be preset and will automatically end if either the first counter or the second counter reaches its predetermined count.

There are, of course, additional features of the invention that will be described hereinafter which will form the subject matter of the appended claims. Those skilled in the art will appreciate that the preferred embodiments may readily be used as a basis for designing other structures, methods and systems for carrying out the several purposes of the present invention. It is important, therefore, that the claims be regarded as including such equivalent constructions since they do not depart from the spirit and scope of the present invention. The foregoing and other features and other advantages of the invention will be apparent from the following more particular description of preferred embodiments of the invention, as illustrated in the accompanying drawings.

DESCRIPTION OF THE PREFERRED EMBODIMENT

Figure 1:
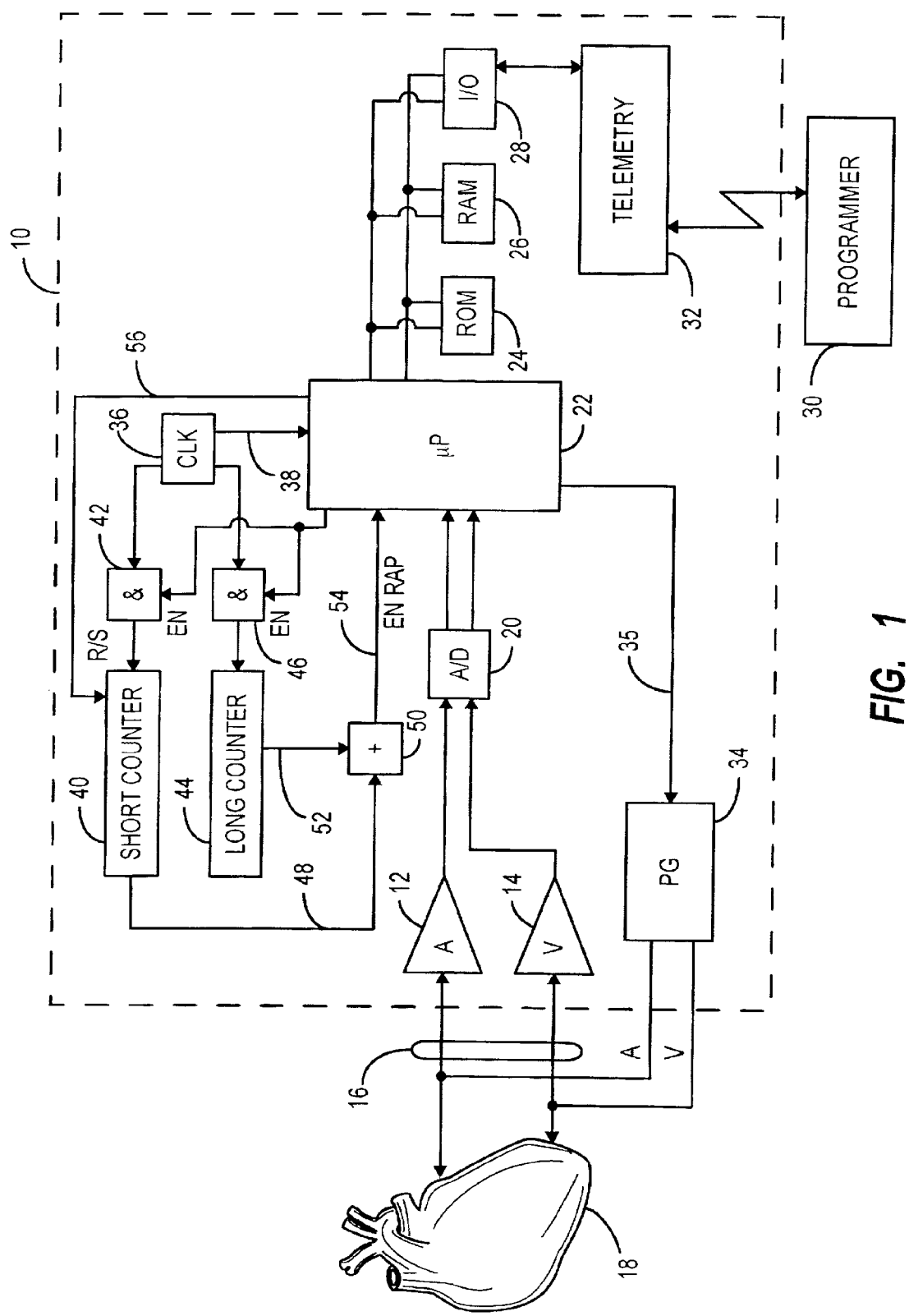
FIG. 1 is a block diagram representation of a cardiac rhythm management device incorporating the present invention.

Referring first to FIG. 1, there is shown enclosed by the dashed-line box 10 a cardiac rhythm management device incorporating the safety circuit of the present invention. The device 10 is seen to comprise an atrial sense amplifier 12 for sensing atrial depolarization signals and a ventricular sense amplifier 14 for sensing ventricular depolarization signals. Leads 16 couple the device 10 to the heart 18 in a fashion well known in the art. The outputs from the atrial sense amplifier 12 and the ventricular sense amplifier 14 are applied, via an analog-to-digital converter 20, to inputs of a microprocessor-based controller 22. Associated with the microprocessor-based controller 22 are a ROM memory 24 which generally stores the program of instructions executable by the microprocessor and a RAM memory 26 that, generally speaking, stores programmable quantities and operands used by the stored program during execution of the instructions stored in the ROM 24. Also coupled to the microprocessor-based controller 22 is an input/output interface 28 allowing duplex communication with an external programmer 30, via a telemetry link 32.

The microprocessor-based controller 22 is connected in controlling relationship to a pulse generator 34, via line 35. Thus, the microprocessor-based controller 22 may control the pulse width, pulse amplitude and time of occurrence of stimulating pulses delivered to the atrial and/or ventricular chambers of the heart 18 by way of the leads 16.

In implementing the safety circuit of the present invention, the same clock circuit 36 that is used to provide timing information to the microprocessor-based controller by way of line 38 may also deliver regularly occurring clock pulses to a first counter labeled "short counter" 40 when the AND gate 42 is enabled. Alternatively, a separate clock may be provided to advance the counter 40. The clock circuit 36 or a separate clock may also be arranged to deliver regularly occurring clock pulses to a second counter labeled "long counter" 44 when the AND gate 46 is enabled. The short counter 40 has an output 48 connected as input to an OR gate 50 and, similarly, the long counter 44 has an output 52 also coupled as an input to the OR gate 50. The output of OR 50 is applied, via line 54, to an appropriate input of the microprocessor-based controller 22. The short counter 40 may also be periodically reset by control signals from the microprocessor-based controller 22 on line 56 under firmware control. Without limitation, the clock rate and the counter lengths of the short counter and long counter may be such that the short counter times out in a range of 500 ms to 2000 ms and the long counter times out in a range from 5 sec. to 60 sec.

In order to test the ability of the implanted pacemaker to terminate a patient's atrial or ventricular tachycardia, pacemakers are designed to allow the clinician to purposely induce a tachycardia episode by using programmed electrical stimulation or manual burst pacing. The response of the pacemaker to the induced episode permits evaluation of its ability to terminate the tachycardia. Because the programmed electrical stimulation or manual burst pacing is at a pulse repetition rate in excess of the pacemaker's runaway protection rate, the runaway protection feature must be disabled to allow these higher rates to be produced by the pulse generator 34. To insure that the runaway protection limiting pacing rate is re-enabled within a predetermined time following its being disabled, the microprocessor 22 applies an enable signal to the AND gates 42 and 46 at the time that the runaway protection (RAP) is disabled. See the timing diagram of FIG. 2. With these two gates enabled, regularly occurring clock pulses from the crystal-controlled clock 36 or an alternative source of clock pulses are applied to both the short counter 40 and the long counter 44. As seen in time line A FIG. 2, if the count value in the short counter reaches a preset value corresponding to the lapse of a predetermined time, say one second, a signal is sent over line 48 and the OR gate 50 and line 54 to again enable the runaway protection feature (en RAP) and to initiate a system fault interrupt.

With reference to time line B in FIG. 2A, however, if the microprocessor 22 is programmed to write a sequence of two specified values to a particular register, the short counter 40 is reset, via signal on line 56. If this happens before the predetermined count value is reached in the short counter, the system fault interrupt is not issued and the time interval for which the runaway protection feature is disabled is extended. If after being extended one or more times, the software does not cause a reset of the short counter, a fault interrupt is generated and the runaway protection feature will again be enabled when the contents of the short counter 40 reach the predetermined count value corresponding to one second in the example given.

Figure 2:
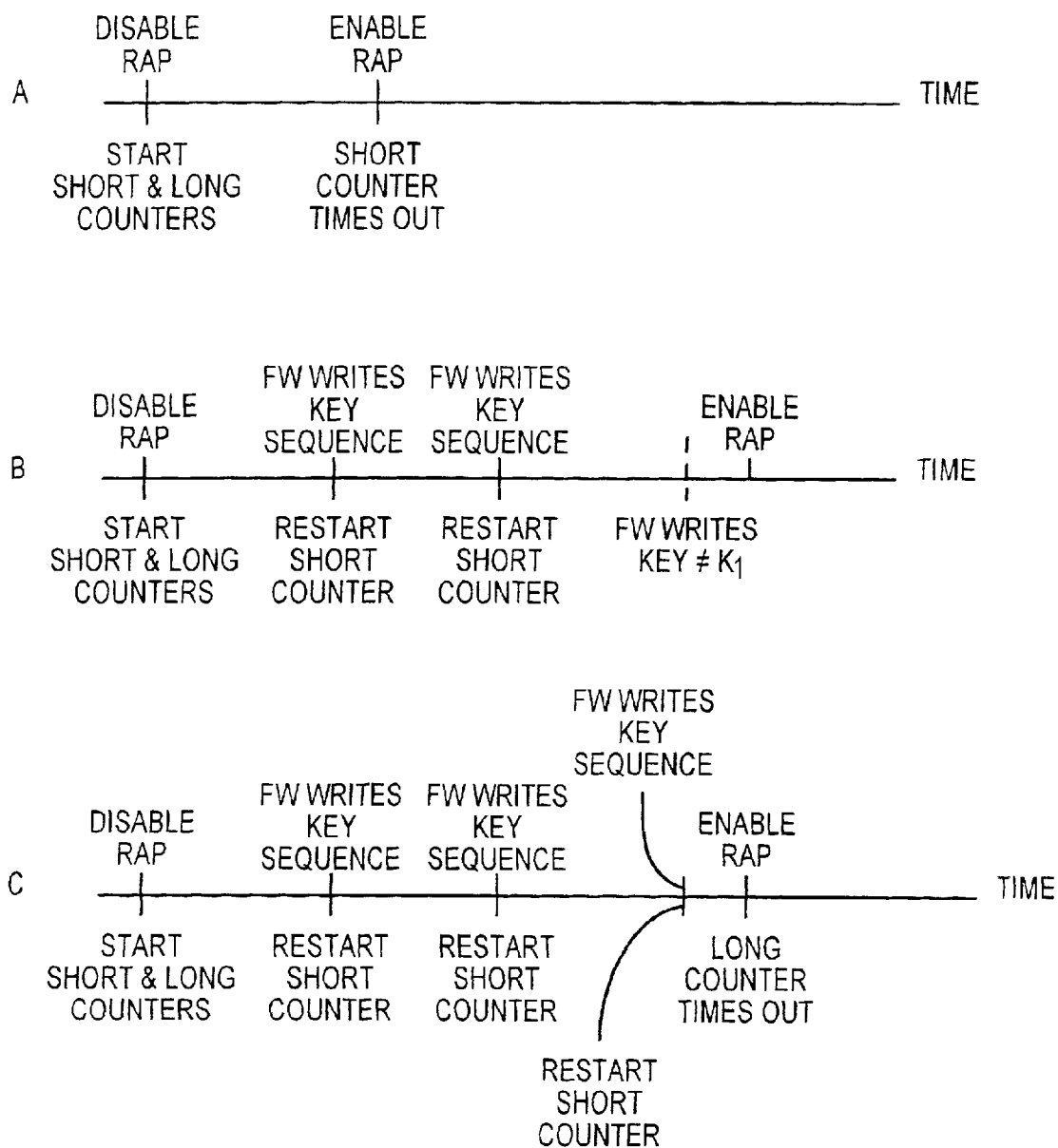
FIG. 2 is a timing diagram useful in understanding the mode of operation of the present invention.

As further illustrated in time line C in FIG. 2, even if the short counter 40 is repeatedly reset due to a firmware error, the runway protection feature will become reenabled upon the count value in the long counter 44 reaching its predetermined value, at which point it feeds the en RAP signal over line 52 to the OR gate 50 which then outputs a signal on line 54 to the microprocessor 22 for re-enabling the runaway protection feature of the device 10. In this way, the long counter provides a hard limit that is not vulnerable to firmware failures.

By providing the additional hardware logic, including the short counter 40 and the long counter 44, the runaway pacing protection may be disabled for an arbitrary amount of time during which programmed electrical stimulation or manual burst pacing can take place, as long as the device firmware has control of the process. But if firmware loses control due to a hardware or firmware defect, runaway pacing protection will not continue to be disabled for an indefinite amount of time and a system fault interrupt will be generated, preventing disabling of the runaway protection until it is cleared by the microprocessor-based controller 22.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself. While the embodiment illustrated in FIG. 1 is for a pacer having a single atrial channel and a single ventricular channel, those skilled in the art will recognize that the timer logic can be applied to pacers having multiple atrial and/or ventricular channels, including biventricular devices, biatrial devices and devices where stimulation is applied to more than one site in a given chamber.

Another modification contemplated is to have the counters 40 and 44 driven by output pulses from the pulse generator 34 during burst pacing rather than by the system's clock 36.

What is claimed is:

1. A cardiac rhythm management device comprising:
   (a) an R-wave sensor for sensing ventricular depolarization events;
   (b) a pulse generator for applying cardiac stimulating pace pulses to the heart of a patient;
   (c) a programmed microprocessor-based controller coupled to the R-wave sensor and to the pulse generator for providing stimulating pace pulses to the heart at times determined by the microprocessor-based controller, the microprocessor-based controller having a runaway pacing protection limit for normally precluding the pace pulse generator from applying the stimulating pace pulses to the heart at a rate greater than said runaway pacing protection;
   (d) means under software control for selectively disabling the runaway pacing protection limit; and
   (e) means responsive to the selective disabling of the runaway pacing protection limit for automatically re-enabling the runaway pacing protection limit a first predetermined time following the disabling of the runaway pacing protection limit.

2. The cardiac rhythm management device as in claim 1 wherein the first predetermined time is extendable up to a second predetermined time.

3. The cardiac rhythm management device as in claim 1 wherein the means responsive to the selective disabling of the runaway pacing protection limit comprises a first counter for counting pulses and for producing a re-enabling signal when the count reaches a first predetermined count value.

4. The cardiac rhythm management device as in claim 3 wherein the microprocessor-based controller can reset the first counter before the first predetermined count value is reached to thereby extend a time that the runaway pacing protection limit remains disabled.

5. The cardiac rhythm management device as in claim 4 wherein the microprocessor-based controller sets the first counter by writing a sequence of two specific values to a specified register.

6. The cardiac rhythm management device as in claim 5 wherein the first counter is made to reach the predetermined count value prematurely and a system fault is declared when a sequence other than the sequence of said two specific values is written to the specified register.

7. The cardiac rhythm management device as in claim 4 and further including a second counter for counting said pulses and producing a signal to re-enable the runaway pacing protection limit upon reaching a second predetermined count value irrespective of the count state of the first counter.

8. The cardiac rhythm management device of claim 7 wherein a system fault is declared upon the second predetermined count value being reached.

9. The cardiac rhythm management device as in either claim 6 or claim 8 wherein the means for selectively disabling the runaway pacing protection limit is suspended until said system fault has been cleared by the microprocessor-based controller.

10. The cardiac rhythm management device as in either claim 3 or claim 7 wherein the pulses are regularly occurring clock pulses from a clock circuit.

11. The cardiac rhythm management device as in either claim 3 or claim 7 wherein the pulses are pace pulses from the pulse generator.

12. The cardiac rhythm management device as in claim 4 and further including means for limiting the number of times the first counter can be reset without re-enabling the runaway pacing protection limit.

* * * * *